United States Patent [19]

Bellis

[11] 4,281,193
[45] Jul. 28, 1981

[54] PROCESS FOR PREPARING SUBSTITUTED FORMAMIDES

[75] Inventor: Harold E. Bellis, Wilmington, Del.

[73] Assignee: E. I. Du Pont de Nemours and Company, Wilmington, Del.

[21] Appl. No.: 169,530

[22] Filed: Jul. 16, 1980

[51] Int. Cl.$^3$ .............................................. C07C 102/00
[52] U.S. Cl. ................................ 564/215; 260/239 A; 260/239 B; 260/326.5 J; 544/386; 546/245; 564/218; 564/219
[58] Field of Search ..................... 564/215, 218, 219; 260/239 A, 239 B, 326.5 J; 544/386; 546/245

[56] References Cited

U.S. PATENT DOCUMENTS

| 2,793,211 | 5/1957 | Locicero | 564/215 |
| 3,483,210 | 12/1969 | Rosenblatt | 564/218 |
| 4,042,621 | 8/1977 | Sauer | 564/215 |

OTHER PUBLICATIONS

Davis, Tet. Letters 1968, #38, pp. 4085–4086.

Primary Examiner—Arthur P. Demers

[57] ABSTRACT

Substituted formamides are prepared by the catalytic oxidation of substituted tertiary amines, in which the catalyst is a metal halide used in conjunction with an alkali metal halide or ammonium halide.

7 Claims, No Drawings

PROCESS FOR PREPARING SUBSTITUTED FORMAMIDES

BACKGROUND OF THE INVENTION

1. Field of the Invention

This invention relates to a process for preparing substituted formamides by the catalytic oxidation of substituted tertiary amines. It is more particularly directed to such a process in which the catalyst is a metal halide used in conjunction with an adjunct which is an alkali metal halide or ammonium halide.

2. Description of the Prior Art and Summary of the Invention

It is well known that substituted formamides can be prepared from tertiary amines by catalytic oxidation. One such method is shown in U.S. Pat. No. 3,483,210 to Rosenblatt and Davis.

Another catalytic oxidation method is shown in U.S. Pat. No. 4,042,621 to Sauer. In that method, a tertiary amine is catalytically oxidized to a corresponding formamide using as the catalyst a soluble chloride, bromide or iodide of cobalt, copper, gold, iron, manganese, mercury, nickel, palladium, platinum, rhenium, silver or zinc.

The Sauer process is an excellent one and gives good conversion of trimethylamine to the commercially desirable dimethylformamide, particularly when copper halides, especially $CuCl_2$, are used as catalysts. As is well known, however, copper halides are quite corrosive to metals such as stainless steel ordinarily used in fabricating chemical processing equipment, and use of the Sauer process in a practical commercial way therefore requires that equipment be made of titanium. Moreover, in the reaction, the copper halides are oxidized to oxyhalides, which are noncatalytic and which are insoluble in the reaction mass and precipitate out. These oxyhalides are difficult to redissolve and so must be removed, which interferes with the continuity of the reaction.

It has now been found, according to the invention, that the corrosion is minimized and that solubility of the catalyst in the reaction medium is generally increased if the catalyst is used in conjunction with an adjunct which is a chloride, bromide or iodide of sodium, potassium, lithium or ammonium. Use of the combination also significantly improves the selectivity of the oxidative conversion of trimethylamine to dimethylformamide.

DETAILED DESCRIPTION OF THE INVENTION

The oxidative reaction proceeds according to the general equation

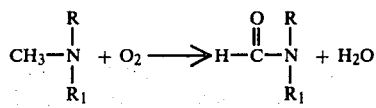

where R and $R_1$ are alkyl radicals of 1–8 carbon atoms, aryl radicals of 6–10 carbon atoms, aralkyl radicals of 7–10 carbon atoms, or alkaryl radicals of 7–10 carbon atoms, and $R_1$ can in addition be an alkyl radical containing a —$N(CH_3)R_2$ group in which $R_2$ can be hydrogen, an alkyl radical of 1–8 carbon atoms, an aryl radical of 6–10 carbon atoms, an aralkyl radical of 7–10 carbon atoms or an alkaryl radical of 7–10 carbon atoms, with the provisos that R and $R_1$ can be joined together to from an alkylene or azaalkylene group of 3–8 carbon atoms, and where R is alkyl or aralkyl, $R_1$ can be hydrogen.

The amine used as a starting material in the reaction can be any which satisfies the formula above, and this amine will give the corresponding formamide, as shown by the equation. The oxidation of trimethylamine to dimethylformamide is preferred.

The oxygen used in the process can be pure or mixed with an inert gas or gases such as air. The use of air is preferred.

The reaction is ordinarily conducted in a liquid medium because the medium helps dissolve the catalyst and helps moderate the exothermic reactions which take place. Any organic liquid which is inert to the reaction in the sense that it does not interfere with it can be used. Illustrative are amides such as methylformamide, dimethylformamide and dimethylacetamide; alkanenitriles such as acetonitrile and propionitrile; alkanols such as methanol, ethanol, isopropanol and butanol; and sulfoxides such as dimethyl sulfoxide. Dimethylformamide is preferred, especially when it is also the product of the reaction, as this eliminates the need for the addition step of removing extraneous solvent at the end of the process.

The catalyst used in the reaction is a soluble chloride, bromide or iodide of copper, cobalt, gold, iron, mercury, nickel, palladium, platinum, silver or zinc. Mixtures can also be used. The catalysts preferred for use are the copper chlorides, especially $CuCl_2$. "Soluble", as used in this context, means that the catalyst dissolves in the reaction medium, usually completely, but always to the extent that it provides a catalytic effect.

The catalyst is used in conjunction with an adjunct which is a chloride, bromide, or iodide of sodium, potassium, lithium or ammonium. Sodium iodide is preferred. Mixtures of adjuncts can also be used.

The catalyst and adjunct are used in proportions which are plus or minus 50% of the equimolar amounts. Equimolar amounts are preferred. More or less of the adjunct can be used, but if less is used the benefits of the invention are not fully realized, and if more is used no additional benefit is obtained.

The catalyst-adjunct combination is ordinarily present in the reaction mass at a concentration of 0.25–20% by weight. The absolute amount of the combination used is not critical, it being important only that a catalytically effective amount be present.

The process of the invention can be run batchwise or in a continuous fashion.

In the batch mode, a reactor is charged with a suitable liquid medium into which is dissolved the desired amount of catalyst-adjunct combination. To the resulting medium is then added 20–40%, by weight of the medium, of the amine. The reactor is then sealed and heated to and held at 25°–150° C., preferably 80°–115° C. Enough oxygen or air is then introduced into the reactor to give an amine/oxygen mole ratio of 1/1.1–1.2 and to maintain a pressure of 344–690 kPa (50–100 psig) if oxygen is used or 2758–3448 kPa (400–500 psig) if air is used. The reaction mass is then agitated until the reaction is finished, normally a matter of 1–2 hours, as signalled by cessation of oxygen absorption.

The reactor is then cooled to ambient temperature, and unreacted oxygen and unreacted amine are vented. The substituted formamide product is then recovered from the reaction mass by conventional distillation techniques.

The process is run continuously in much the same fashion. A reactor is charged with the liquid medium and the desired amount of catalyst-adjunct combination. The reactor is then pressurized with oxygen or air, and the amine and oxygen or air are fed into the reactor in such amounts that the amine/oxygen mole ratio is held within the range 1/1.05-1.2 and the pressure is maintained at 344-610 kPa if oxygen is used and 2758-3448 kPa if air is used. The temperature of the reactor contents is held within the range 25°-150° C., preferably 80°-115° C., and the residence time of the reaction mass in the reactor should be about ½-1 hour, preferably ¾ hour.

The effluent from the reactor is fed to a separator, where the pressure is released and the gases vented. Substituted formamide product is obtained from the remaining liquid by conventional distillation procedures.

In the following examples, all percentages are by weight.

EXAMPLES

Example 1 (Best Mode)

A titanium pressure reactor was filled to 80% of its capacity with a charge of

| Dimethylformamide | 98.1% |
|---|---|
| CuCl$_2$ | 1.0% |
| NaI | 0.9% |

The charge was heated to and held at a temperature of 115° C., with stirring. The reactor was then sealed and pressurized with air to 3448 kPa gauge (500 psig), and air was continuously fed in to maintain this pressure.

Trimethylamine was then continuously fed into the reactor at a rate which maintained an oxygen/trimethylamine mole ratio of 1/1.08, as determined with flow meters. Residence time of the trimethylamine in the vessel was 45 minutes.

Overflow from the reactor was continuously fed to an enclosed separator, where gases were removed from the top and liquid crude dimethylformamide removed from the bottom.

After 15 hours of operation, all of the catalyst system remained in solution and stainless steel coupons (18% chromium, 8% nickel and 74% iron) in the reactor showed a corrosion rate of 152 microns (6 mils) per year, a commercially acceptable rate.

EXAMPLES 2

A titanium pressure reactor was charged with

| Trimethylamine | 20 parts |
|---|---|
| Dimethylacetamide | 40 parts |
| CuI | 6 parts |
| KI | 6 parts |

The reactor was sealed and its contents heated to and held at 105° C., with continuous shaking. Oxygen was then fed into the vessel to a pressure of 690 kPa gauge (100 psig). When the pressure had fallen to 345 kPa gauge (50 psig), it was brought back to 690 kPa. This was done repeatedly until there was no more pressure drop, a matter of about 2 hours. Pressure was then released by venting the oxygen, and the reaction product, crude dimethylformamide, was recovered by distillation. The catalyst system remained in solution.

After 120 hours of use, stainless steel coupons (18% chromium, 8% nickel and 74% iron) in the reactor showed a corrosion rate of 280 microns (11 mils) per year, a commercially acceptable rate.

I claim:

1. A process for the catalytic preparation of a substituted formamide, the process comprising
(A) bringing together, in an inert liquid medium, under conditions suitable for reaction,
(1) a compound represented by the structure

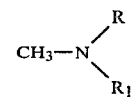

where
R and R$_1$ *are alkyl radicals of* 1-8 carbon atoms, aryl radicals of 6-10 carbon atoms, aralkyl radicals of 7-10 carbon atoms or alkaryl radicals of 7-10 carbon atoms, and R$_1$ can in addition be an alkyl radical containing a —N(CH$_3$)R$_2$ group in which R$_2$ can be hydrogen, an alkyl radical of 1-8 carbon atoms, an aryl radical of 6-10 carbon atoms, an aralkyl radical of 7-10 carbon atoms or an alkaryl radical of 7-10 carbon atoms, with the provisos that R and R$_1$ can be joined together to form an alkylene or azaalkylene group of 3-8 carbon atoms, and when
R is alkyl or aralkyl, R$_1$ can be hydrogen;
(2) oxygen; and
(3) a catalytically effective amount of a combination of
(a) a soluble chloride, bromide or iodide of copper, cobalt, gold, iron, mercury, nickel, palladium, platinum, silver or zinc, and
(b) a chloride, bromide or iodide of sodium, potassium, lithium or ammonium, and then
(B) recovering the substituted formamide product from the reaction mass.

2. The process of claim 1 wherein the compounds in (3) (a) and (3) (b) are present in proportions which are ±50% of the equimolar amount.

3. The process of claim 1 wherein the compound in (A) (1) is trimethylamine.

4. The process of claim 1 wherein the compound in (3) (a) is cupric chloride and the compound in (3) (b) is sodium iodide.

5. A process for catalytically preparing dimethylformamide from trimethylamine, the process comprising bringing together, in an inert liquid medium, under conditions suitable for reaction,
(A) trimethylamine,
(B) oxygen, and
(c) a catalytically effective amount of a combination of cupric chloride and sodium iodide, in ±25% of the equimolar amount,
and then recovering dimethylformamide from the reaction mass.

6. The process of claim 5 wherein the inert liquid medium is dimethylformamide.

7. The process of claim 5 wherein the cupric chloride and sodium iodide are present in about equimolar amounts.

* * * * *